(12) United States Patent
Luo et al.

(10) Patent No.: US 7,561,267 B2
(45) Date of Patent: Jul. 14, 2009

(54) FLOW CYTOMETER

(75) Inventors: Cheng Luo, Shenzhen (CN); Hanrong Shao, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 0 days.

(21) Appl. No.: 11/615,651

(22) Filed: Dec. 22, 2006

(65) Prior Publication Data

US 2008/0079929 A1   Apr. 3, 2008

(30) Foreign Application Priority Data

Sep. 30, 2006   (CN)   .................. 2006 1 0062982

(51) Int. Cl.
G01N 15/02   (2006.01)

(52) U.S. Cl. ......................... 356/336; 356/73

(58) Field of Classification Search ......... 356/336–338, 356/317–318; 436/10, 52, 63, 164, 165, 436/172; 422/73, 81, 82.05–82.09
See application file for complete search history.

(56) References Cited

U.S. PATENT DOCUMENTS

| | | | |
|---|---|---|---|
| 4,990,795 A | | 2/1991 | Suzuki et al. |
| 5,013,120 A | * | 5/1991 | Gergely et al. ................ 385/33 |
| 5,142,462 A | | 8/1992 | Kashima |
| 6,707,555 B1 | | 3/2004 | Kusuzawa et al. |
| 6,713,019 B2 | * | 3/2004 | Ozasa et al. ............. 422/82.09 |
| 7,110,192 B2 | | 9/2006 | Sauter et al. |
| 7,441,703 B2 | * | 10/2008 | Moon et al. .................. 235/454 |
| 7,468,789 B2 | * | 12/2008 | Czarnek ...................... 356/246 |
| 2003/0142720 A1 | * | 7/2003 | Bradburn et al. ............. 372/108 |
| 2005/0105077 A1 | * | 5/2005 | Padmanabhan et al. ....... 356/39 |

FOREIGN PATENT DOCUMENTS

CN   1712926 A   12/2005

OTHER PUBLICATIONS

China patent application No. 200610062982.2, search report dated Nov. 7, 2006.

* cited by examiner

*Primary Examiner*—Tarifur Chowdhury
*Assistant Examiner*—Jonathon D Cook
(74) *Attorney, Agent, or Firm*—Vista IP Law Group, LLP (57) ABSTRACT

The present invention relates to a flow cytometer, comprising a light source, a light beam shaping module for collimating and converging a light beam emitted from the light source so that the light beam irradiates samples to be detected, a sample generation unit, which comprises a gas-liquid transmission controlling module and a flow chamber that are interconnected, and a signal processing unit, for collecting, photoelectrically converting and analyzing the scattered beam emitted from the flow chamber. The light beam shaping module comprises a first cylindrical lens and a second cylindrical lens for respectively converging the light beams in two directions. In the present invention, the spot converged at the cell-interrogation zone of the flow chamber is flattened to avoid instability of the fluid which in turn leads to instability of the excited optical signal, and consequently the stability and reliability of the system are improved.

16 Claims, 9 Drawing Sheets

FLOW CYTOMETER

RELATED APPLICATION

The present application claims the priority of the Chinese Patent Application No. 200610062982.2, titled "FLOW CYTOMETER", which was filed on Sep. 30, 2006, and is incorporated herein by reference in its entirety.

FIELD OF THE INVENTION

The present invention relates to a cytometer, in particular, to a flow cytometer.

BACKGROUND OF THE INVENTION

Cytometers, as an instrument for counting and classifying various cells, have been widely used in the medical and biological fields. Conventional cytometers typically employ a flow cytometry. Such a cytometer is comprised of a light source, a flow chamber and a photoelectric detection unit. The flow chamber provides an optical cell-interrogation zone, in which a sample flow of cells is encircled in a sheath flow according to the sheath flow principle (i.e., fluid focusing principle), so that the cells pass through the detection passage one by one. The light source, usually a laser, provides an illuminating light beam which may irradiate into the cell-interrogation zone of the flow chamber, such that the illuminating light beam may irradiate onto the cells (e.g., blood cells) flowing through the detection zone so as to be scattered, or excite fluorescence emission, etc. The photoelectric detection unit is useful for collecting various optical information generated in the flow chamber and converting it into electric signals. By processing and analyzing these converted electric signals, the parameters of various cells contained in the blood can be obtained in order for subsequent processing such as counting and classification, etc.

Normally, certain properties of cells are all represented by the peak or pulse width of the signals described above, and thus it is necessary to obtain such data as the peak or pulse width of various optical information. Some desired parameters concerning the blood cells may therefore be calculated by using a histogram or scattergram plotted with these data.

Figure 1:
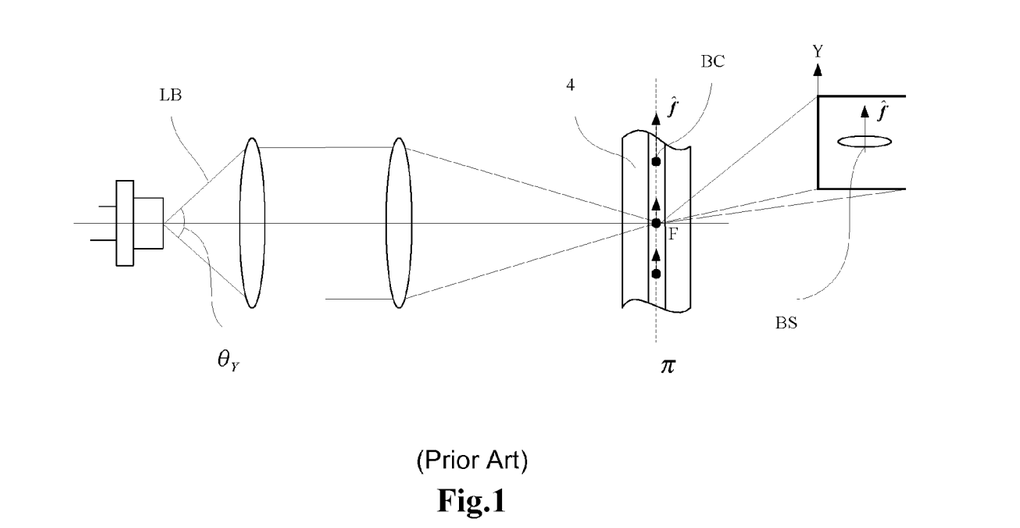
FIG. 1 is a schematic view of a flow cytometer in prior art.

In prior art, for facilitating the blood cells passing through the optical cell-interrogation zone to be detected, the light beam should radiate into the interrogation zone of the flow chamber so as to form a spot, as shown in FIG. 1, the light beam LB, eradiated from a light source, is focused on the center of the cell-interrogation zone of the flow chamber 4 by an optical system, forming an elliptical spot BS on a plane $\pi$ perpendicular to the optical axis at the center of the cell-interrogation zone. The minor axis of the spot should coincide with the flowing direction f of the sample flow. Therefore a light beam shaping module is provided behind the light source, which is used for shaping the beam emitted from the light source, including collimating and converging the light beam. In prior art, light beams are converged by a normal spherical lens. However, in the case of this convergence, the energy distribution of the optical field converged at the cell-interrogation zone of the flow chamber is relatively narrow, with the typical value of 20 μm (minor axis)×80 μm (major axis). Moreover, the direction of the minor axis is the same as the flowing direction of the sample flow in the flow chamber, while the direction of the major axis is perpendicular to the plane defined by the flowing direction of the sample and the transmitting direction of the light beam. Such an energy distribution goes against the stability of signal detection and high-speed cell-interrogation. When the routes via which the cell particles flow through the interrogation zone become chaotic due to an increase in detection rate or other causes, the cell flow may deviate from the energy center of the focused spot, leading to a weakening of the photoelectrically detected signal. As a further result, the scattergram of the detected signals may be subjected to a false appearance, which may affect the accuracy of counting and classification.

Figure 2:
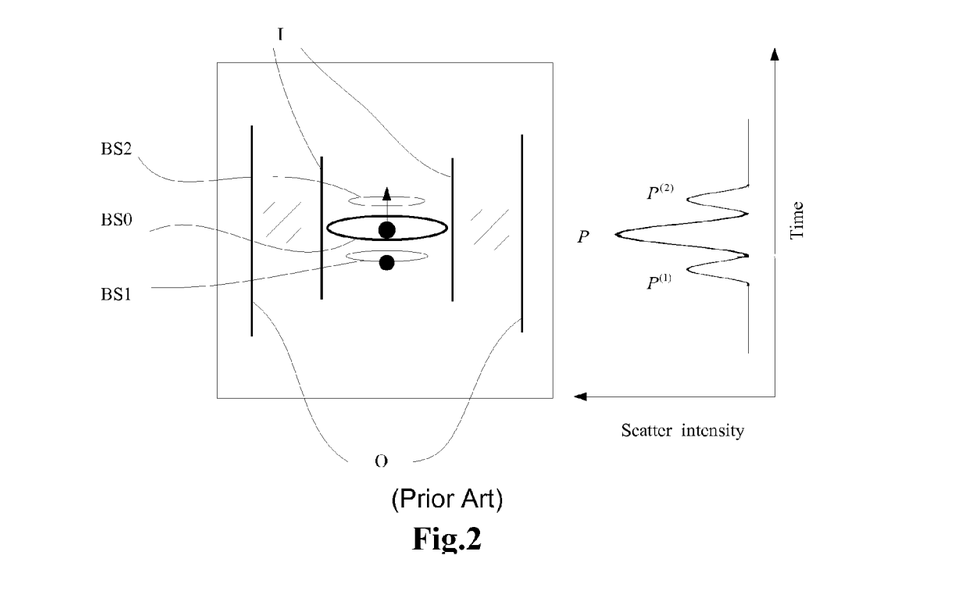
FIG. 2 is a schematic view illustrating the defect of a scattered signal in prior art.
Figure 3:
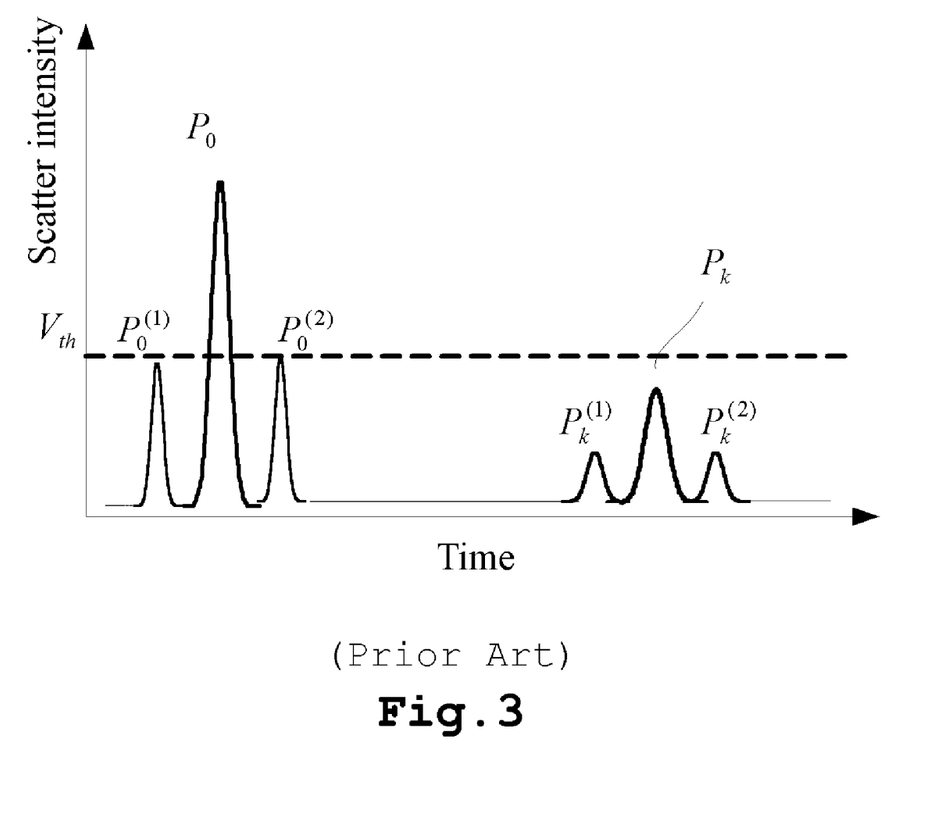
FIG. 3 is a schematic view illustrating a method of eliminating an accompanying pulse using a threshold value in prior art.

Another problem with the prior art cytometer is as follows. In principle, an ordinary spherical Lens is adopted in prior art. Thereby, the collimation concerned is achieved by locating the light source at the focus of such a lens. However, the light beam has a very large angle of divergence in the direction of cell flow if the laser is positioned as shown in FIG. 1, and when the ordinary spherical lens is converging the light beam having a relatively large angle of divergence (non-adaxial) which is emitted from the points on the optical axis, it is not a dot that is converged onto the optical axis, but instead a blurry spot. In other words, light with a different height from the optical axis are converged to different locations, so a significant aberration occurs after the light beam passes through the optical system. As a result, in addition to a main spot BS0, the spot focused at the cell-interrogation zone of the flow chamber further has two symmetrical sidelobes BS1 and BS2, in which I denotes the inner wall of the flow chamber and O the outer wall of the flow chamber, as shown in FIG. 2. Thereby, the signal genenerated by the cells having passed through such an illuminated region will correspondingly comprise sidelobes $P^{(1)}$ and $P^{(2)}$ at both sides of the main pulse signal P. If the amplitudes of these pulses should also be identified as a scattered signal of the cells, the result of the sample detection would be incorrect. In a prior art approach for resolving this problem, a scattered pulse signal recognition algorithm is in principle incorporated in the signal processing unit. That is, a threshold value is made use of to get rid of an accompanying signal. Specifically, when a peak is recognized smaller than a threshold value, it is thereby deemed to be a false accompanying signal and gets rejected, as shown in FIG. 3. However, this approach still has a significant disadvantage in that the main pulse of some smaller cells is usually even smaller than the accompanying pulse of the bigger cells, and consequently the real scattered signal of the small cells would be rejected along with the accompanying pulse of the bigger cells by using the threshold value, which will bring error to the cell analysis.

SUMMARY OF THE INVENTION

The main object of the present invention is to overcome a prior art problem, that is, the distribution of the optical energy in the cell-interrogation zone of the flow chamber is relatively narrow. Specifically, the present invention aims to provide a flow cytometer, which is capable of distributing the energy of the focused spot substantially uniformly along the direction of the major axis, so as to enhance the stability of optical signals excited by the cells. Another object of the present invention is to provide an optical system for use in the flow cytometer, whereby the accompanying signal of the scattered signals may be eliminated by collimating the light beam.

According to the first aspect of the present invention, there is provided a flow cytometer, comprising: a light source, a light beam shaping module for collimating and converging a light beam emitted from the light source so that the light beam irradiates samples to be detected; a sample generation unit, which comprises a gas-liquid transmission controlling module and a flow chamber that are interconnected, so that the sample liquid containing cells to be detected flows through the flow chamber while being encircled by sheath fluid; and a signal processing unit, for collecting, photoelectrically converting, analyzing a scattered beam emitted from the flow chamber and outputting analysis results thereof. The light beam shaping module comprises a first cylindrical lens and a second cylindrical lens for respectively converging the light beams in two directions.

Preferably, the converging directions of the first and second cylindrical lenses are perpendicular to each other. The first cylindrical lens converges the light beam in the flowing direction of the sample flow, which is a positive cylindrical lens or a combination of more than one positive cylindrical lens, or a combination of more than one positive cylindrical lens with more than one negative cylindrical lens. The second cylindrical lens converges the light beam in the direction perpendicular to the plane defined by the flowing direction of the sample flow and the transmitting direction of the light beam, which is a positive cylindrical lens or a combination of more than one positive cylindrical lens, or a combination of more than one positive cylindrical lens with more than one negative cylindrical lens. The converged focus of the first cylindrical lens lies on the sample flow, while the converged focus of the second cylindrical lens is deviated from the sample flow.

The light beams converged by the first and second cylindrical lenses have the cross section of an elliptical spot in the cell-interrogation zone of the flow chamber. The minor axis of the ellipse spot is about 15 μm-25 μm long, and the major axis is about 160 μm-220 μm long. Further, the direction of the minor axis coincides with the flowing direction of the sample flow within the flow chamber, and the direction of the major axis is perpendicular to the plane which is defined by the flowing direction of the sample flow and the transmitting direction of the light beam. The irradiation depth of the light beams is about 8 μm-12 μm, and the light intensity is uniformly distributed at a segment in the direction of the major axis. Furthermore, the major axis of the elliptical spot has a length that is substantially equal to the width of the inner wall of the cell-interrogation zone of the flow chamber.

Optionally, the light beam shaping module further comprises at least one first aspheric collimating lens with a large numerical aperture, which lens is disposed on the light path running from the light source to the cylindrical lens. The numerical aperture of the first aspheric collimating lens is at least 0.3. The first aspheric collimating lens comprises a first lens surface and a second lens surface, wherein the first lens surface denotes the surface that the incident beam impinges on. The lens surfaces of the first aspheric collimating lens satisfy the following formula:

$$z = \frac{cr^2}{1+\sqrt{1-(1+k)c^2r^2}} + \alpha_1 r^2 + \alpha_2 r^4,$$

in which c is the curvature, z is the axial distance of the cross-section from a fixed point, k is a quadratic constant, and r is the radius of the cross-section. The parameters of the first lens surface and second lens surface are as follows:

As to the flow cytometer according to the first aspect of the present invention, the signal processing unit comprises a photoelectric detection module, a signal processing module and an analysis module which are connected in series. The photoelectric detection module is useful for collecting the scattered light in different angle ranges onto the photoelectric converter, so that the optical information out of the scattered light is converted into a corresponding electrical signal which is then sent to the signal processing module. The signal processing module is useful for extracting the peak or pulse width information from the signal and sending the information to the analysis module. The analysis module is useful for counting and classifying the received signals to form a one-dimensional histogram or two-dimensional scattergram.

The photoelectric detection module comprises two sets of photoelectric signal collecting sub-modules for respectively collecting optical signals with different scattering angles, and corresponding photoelectric converters for converting the optical signals into corresponding electrical signals.

Optionally, the photoelectric detection module comprises at least one second aspheric collimating lens for collimating the scattered light emitted from the flow chamber, the numerical aperture of which lens is at least 0.4.

According to the second aspect of the present invention, there is provided an optical system for use in a flow cytometer, comprising a light source, a light beam shaping module for collimating and converging a light beam emitted from the light source. The light beam shaping module comprises a first cylindrical lens and a second cylindrical lens for respectively converging the light beams in two directions.

Preferably, the converging directions of the first and second cylindrical lenses are perpendicular to each other. The first cylindrical lens is a positive cylindrical lens or a combination of more than one positive cylindrical lens, or a combination of more than one positive cylindrical lens with more than one negative cylindrical lens. The second cylindrical lens is a positive cylindrical lens or a combination of more than one positive cylindrical lens, or a combination of more than one positive cylindrical lens with more than one negative cylindrical lens. The converged focus of the first cylindrical lens deviates from that of the second cylindrical lens.

The light beams converged by the first and second cylindrical lenses have the cross section of an elliptical spot in the converging zone. The minor axis of the ellipse spot is about 15 μm-25 μm long, and the major axis is about 160 μm-220 μm long. The irradiation depth of the light beams is about 8 μm-12 μm, and the light intensity is uniformly distributed at a segment in the direction of the major axis.

Optionally, the light beam shaping module further comprises at least one aspheric collimating lens with a large numerical aperture, which is disposed on the light path running from the light source to the cylindrical lens. The numerical aperture of the aspheric collimating lens is at least 0.3.

The collimating lens comprises a first lens surface and a second lens surface, wherein the first lens surface denotes the surface that the incident beam impinges on. The lens surfaces of the aspheric collimating lens satisfy the following formula:

|  | c | k | α1 | α2 |
|---|---|---|---|---|
| the first lens surface | 0.068609 | −87.228063 | 9.15754E−04 | −8.64353E−05 |
| the second lens surface | −0.23148106 | −0.648067 | −1.65853E−04 | 8.28138E−06 |

$$z = \frac{cr^2}{1 + \sqrt{1 - (1+k)c^2 r^2}} + \alpha_1 r^2 + \alpha_2 r^4,$$

in which c is the curvature, z is the axial distance of the cross-section from a fixed point k is a quadratic constant, and r is the radius of the cross-section. The parameters of the first lens surface and second lens surface are as follows:

|  | c | k | α1 | α2 |
|---|---|---|---|---|
| the first lens surface | 0.068609 | −87.228063 | 9.15754E−04 | −8.64353E−05 |
| the second lens surface | −0.23148106 | −0.648067 | −1.65853E−04 | 8.28138E−06 |

Preferably, the light source is a semiconductor laser.

The advantages of the present invention are as follows.

(1) The present invention employs two sets of cylindrical lens to respectively converge the light beam in two directions, so that the lens parameters in one direction can be flexibly adjusted without affecting the convergence in the other direction, whereby the spot may be flattened in a certain direction.

(2) The present invention takes advantage of two positive cylindrical lenses to converge the collimated light beam. The first cylindrical lens converges the light beam in the flowing direction of the sample flow to an extent of 15 μm-25 μm within the cell-interrogation zone of the flow chamber. The second cylindrical lens converges the light beam in the direction perpendicular to the sample flowing direction. However, the converged focus thereof is not on the sample flow, but deviates therefrom, so as to ensure that the dimension of the converged light beam in the cell-interrogation zone of the flow chamber is within 160 μm-220 μm. Thus the light beam is converged only in these two directions. Further, by adjusting the focal length, the major axis of the spot is much longer than the minor axis, so that the light intensity is uniformly distributed at a segment in the direction of the major axis, whereby flattening of the spot is achieved. Therefore, when the cells are deviated from the sample flow due to some disturbance, the energy of the light beam excited by the cells remains constant. That is, instability of the flow will not lead to instability of the excited optical signal, thus the stability and reliability of the system are improved.

(3) By using an aspheric lens with a large numerical aperture in the present invention, the light beam with a large scattering angle could be collimated successfully. Thereby, the optical system according to the present invention is capable of eliminating the sidelobes of the irradiating spot at the cell-interrogation zone of the flow chamber and avoiding the disturbance of the false pulse of the scattered signal, which renders the result of the detection more accurate. The realization of such accuracy is ensured by the design of the optical system, which is an intrinsic feature, without a need in signal processing for related elimination, so that signal processing becomes simpler and more direct, providing the present invention with improved practicability.

The features and advantages of the present invention will be explained in greater details by way of embodiments in conjunction with the accompanying drawings.

DETAILED DESCRIPTION OF THE INVENTION

EXAMPLE 1

Figure 4:
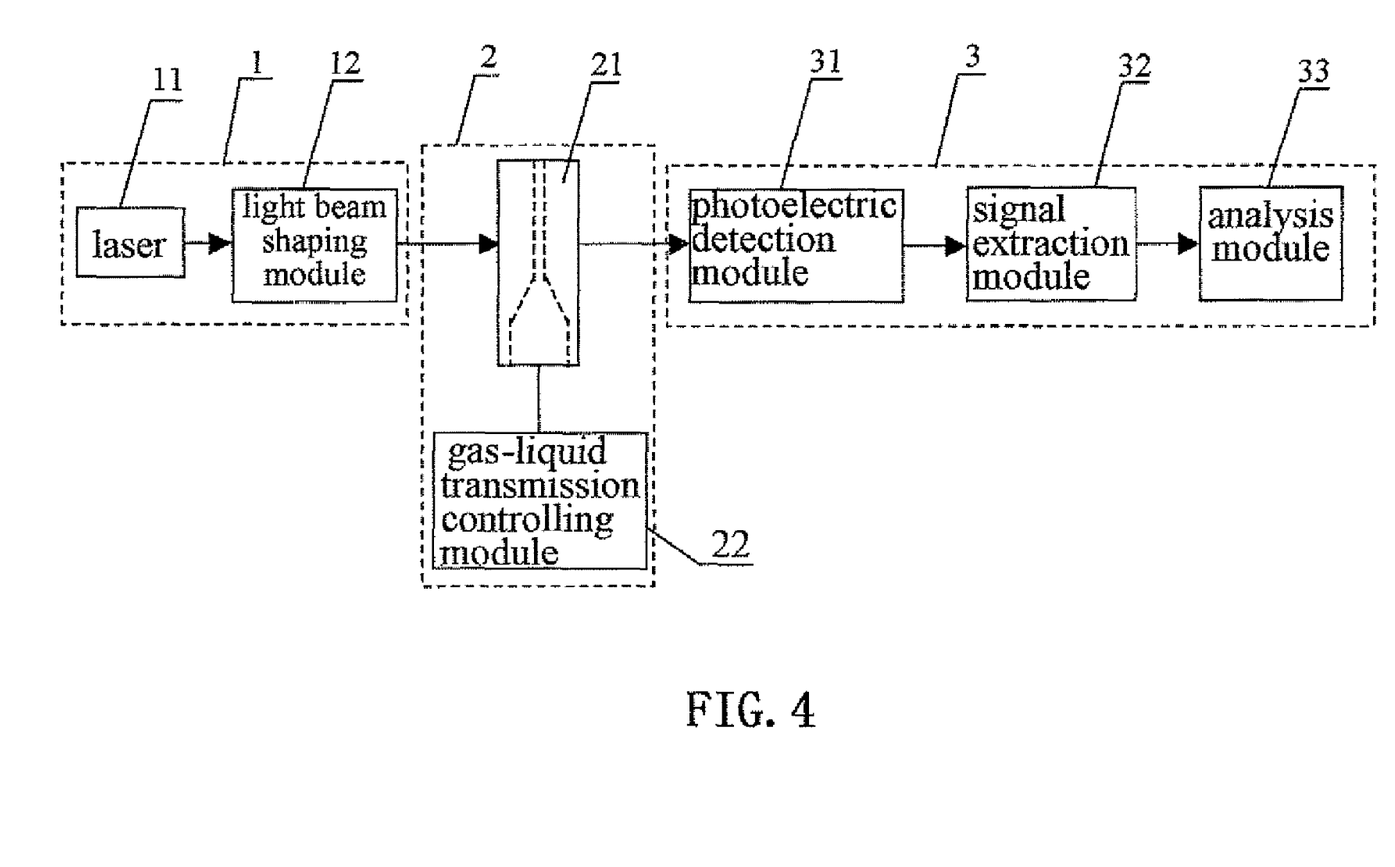
FIG. 4 is a schematic view showing the structure of the system according to an embodiment of the present invention.

As shown in FIG. 4, the flow cytometer according to the present embodiment comprises an illuminating unit 1, a sample generation unit 2 and a signal processing unit 3 which are connected in series.

Figure 5:
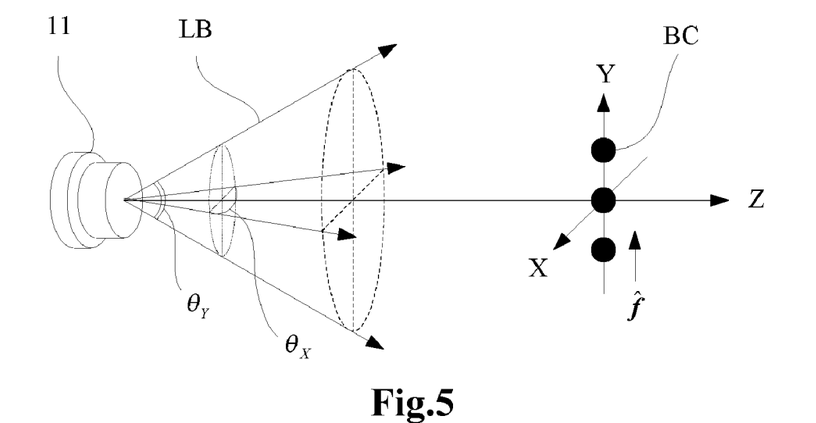
FIG. 5 is a schematic view showing the light beam emitted from the semiconductor laser according to the embodiment of the present invention, and the orientation of that laser.

The illuminating unit 1 comprises a light source and a light beam shaping module 12. The light source is typically a laser 11 such as a gas laser or solid laser, and preferably, a semiconductor laser in the present embodiment, which significantly reduces the structural dimension of the whole system. As shown in FIG. 5, the light beam LB emitted by the semiconductor laser has different divergence angles in two directions. Assuming that the light is transmitted along Z axis, the light beam divergence angle θx in the X direction does not equal to the divergence angle θy in the Y direction. If θx<θy, then the section of the light beam would be an elliptical spot with the major axis in the Y direction. At the time of disposing the semiconductor laser, the orientation of the smaller divergence angle of the original exit light beam of the semiconductor laser should be kept consistent with the flowing direction of the cell BC, so that the spot will have a relatively small dimension (i.e., minor axis) in the cell flowing direction. As shown in FIG. 5, assuming that the cell flows along Y direction, then it should meet the condition that θx<θy when disposing the semiconductor laser. In the present embodiment, the divergence angles of the light beam emitted from the laser 11 in the two directions perpendicular to each other are 30° and 18° respectively, with a maximum output power of 10 mW, operating power of 5 mW and wavelength of 670 nm.

Figure 6:
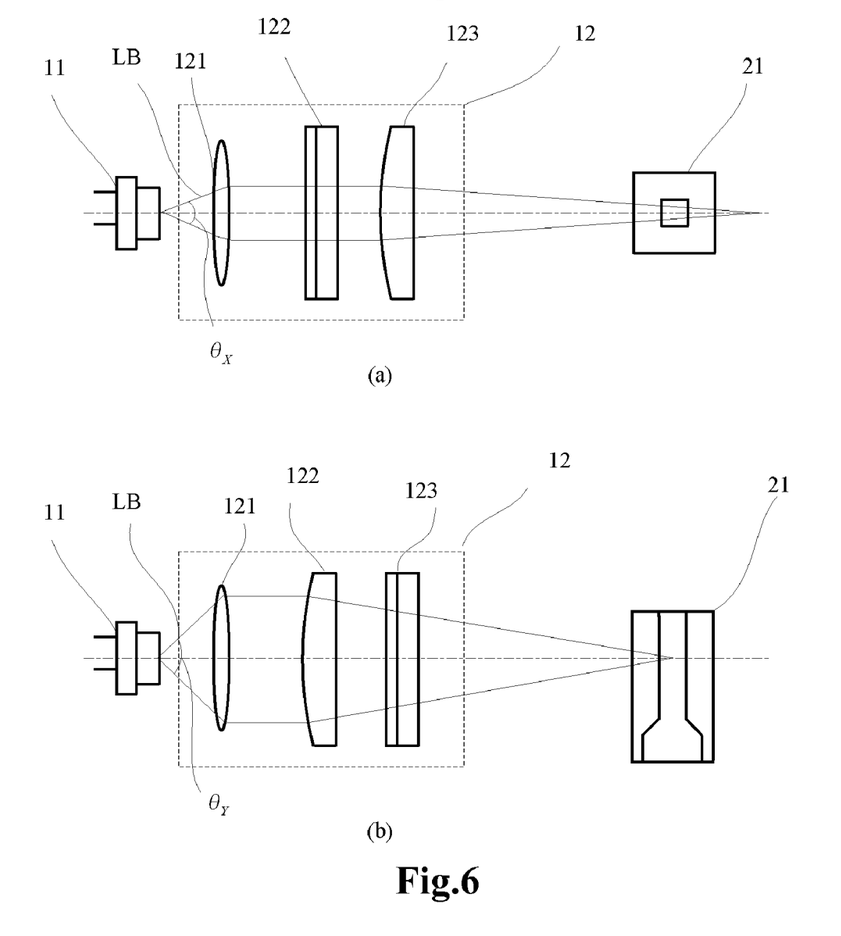
FIG. 6 is a view showing the light path of how the light beam from the semiconductor laser is focused according to the embodiment of the present invention.

The light beam shaping module 12 is used for collimating and converging the laser light beam LB emitted from the laser 11. As shown in FIG. 6, the light beam shaping module 12 comprises at least one piece of collimating lens 121 and a first cylindrical lens 122 and a second cylindrical lens 123, which are perpendicular to each other in terms of the convergence direction. The lenses are functional as sending out a light beam with an elliptical cross section onto the cells flowing through the cell-interrogation zone of the flow chamber 21. The first and second cylindrical lenses are preferably positive cylindrical lenses. As light rays have been rendered parallel through the collimating lens, a positive cylindrical lens may be used directly herein to converge the light. The first and second cylindrical lenses may also be a combination of more than one positive cylindrical lens, or a combination of more than one positive cylindrical lens and more than one negative cylindrical lens, so long as the combined effect thereof is to converge the light. In case the first and second cylindrical lenses are a combination of a plurality of lenses, the lenses included in the combination may be integrated as a whole, or may be separate lenses, and moreover the lenses in two different directions may be spaced apart. The first cylindrical lens converges the light beam in the sample flowing direction (i.e., Y direction), as shown in FIG. 6(*b*), while the second cylindrical lens converges the light beam in the direction perpendicular to the plane defined by the sample flowing direction and the transmitting direction of the light beam (i.e., X direction), as shown in FIG. 6(*a*). Since the light beam is converged respectively from two directions, the first and second cylindrical lenses may be successively arranged as in FIG. 6, or the second cylindrical lens 123 may be arranged in front of the first cylindrical lens 122.

The divergent Gauss beam emitted from the semiconductor laser 11 is so focused at the interrogation zone of the flow chamber 21 that the cross section of the light beam in the interrogation zone is an elliptical spot. Further, the direction of the minor axis is coincident with the sample flowing direction, and the dimension of the minor axis matches with the size of the cells, whereby it is ensured that the cells pass through the interrogation zone individually. The direction of the major axis of the spot is perpendicular to the sample flowing direction and the direction of the optical axis, i.e., X direction. To flatten the spot in X direction, the converged focus of the first cylindrical lens should lie on the sample flow, while that of the second cylindrical lens should deviate from the sample flow, e.g., in front of or behind the sample flow, but remains on the optical axis. Thus, the cross section of the light beam converged by the first and second cylindrical lenses is an elliptical spot in the interrogation zone of the flow chamber. The minor axis of the elliptical spot is about 15 μm-25 μm long and the major axis is about 160 μm-220 μm long. The direction of the minor axis coincides with the sample flowing direction within the flow chamber, and the direction of the major axis is perpendicular to the plane which is defined by the sample flowing direction and the transmitting direction of the light beam. The irradiation depth of the light beam is about 8 μm-12 μm, and the light intensity is uniformly distributed for a certain distance in the direction of the major axis. The dimension of the major axis is such that the spot should cover as much as possible the flow chamber in the width direction of the inner wall of the flow chamber interrogation zone. However, if the spot is too wide, the energy of the laser may be affected, and correspondingly, the scattered light may be relatively weak, which will put the subsequent signal processing into an awkward position. The parameters of the positive cylindrical lens, such as focal distance, radius of curvature and thickness etc., may be determined according to the actual focusing length and the dimension of the focused spot. The cylindrical lens may be deemed as the lens that converges or diverges light beams in one direction, the detailed calculation concerning which may refer to the transformation formula of the Gauss light beam through the lens. Generally, the following formula may be used for approximate calculation:

$$\delta = \frac{4f\lambda}{\pi d}$$

wherein: δ is the dimension of the focused spot, f is the focal distance of the lens, λ is the wavelength of the incident light, and d is the diameter of the incident light beam.

Figure 7:
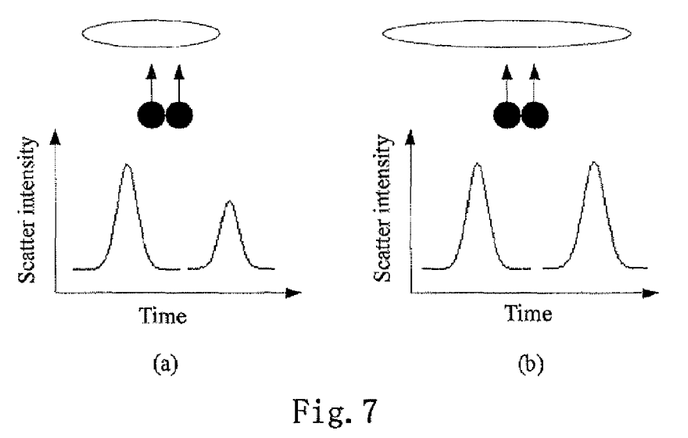
FIG. 7 is a schematic view showing a comparison between the cells' scattered signals in case of an ordinarily focused spot and those in case of a flattened spot.

FIGS. 7(*a*) and (*b*) show a comparison between the cells' scattered signals in case of an ordinarily focused spot and those in case of a flattened spot. FIG. 7(*a*) shows the cells' scattered signal in case of an ordinarily focused spot. In this case, when the cells are deviated from the center of the sample flow, the scattered signal thereof is weakened relative to the scattered signal generated by the cells in the center of the sample flow, as a result of which the signal is unstable. FIG. 7(*b*) shows the cells' scattered signal in case of a flattened focused spot. In the latter case, when the cells are deviated from the center of the sample flow, the scattered signal thereof is substantially unchanged relative to the scattered signal generated by the cells in the center of the sample flow, as a result of which the signal is stable and the detection stability is improved.

Figure 8:
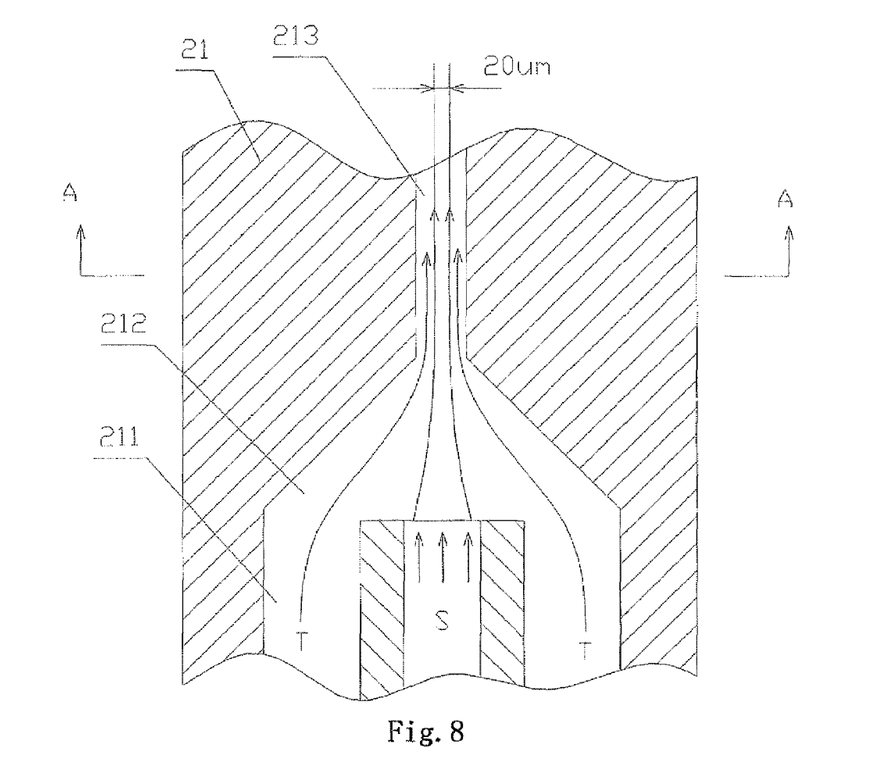
FIG. 8 is a partial view showing the horizontal section of the flow chamber according to the embodiment of the present invention.

As shown in FIG. 4, the sample generation unit 2 comprises a gas-liquid transmission controlling module 22 and a flow chamber 21 which are interconnected. The gas-liquid transmission controlling module 22 is used for carrying out the pneumatic transmission of the sample, the sheath fluid, various reagents, cleaning liquids and waste liquids, and at the same time controlling the various light-sample interaction conditions for the sample liquid, so that the sample liquid containing the cells to be detected may flow through the flow chamber 21 while being encircled by the sheath fluid. As shown in FIG. 8, the flow chamber 21 is made of quartz glass, in the shape of an elongated prism with the dimension of 4 mm×4 mm×10 mm. A guiding hole with a square cross section is provided in the flow chamber 21. The outer wall of the flow chamber 21 and the inner wall of the guiding hole should be sufficiently parallel with each other, and each of them should have excellent flatness and surface quality, so that little changes would occur to the transmitting properties of the light beam when the light beam passes through the flow chamber.

Figure 9:
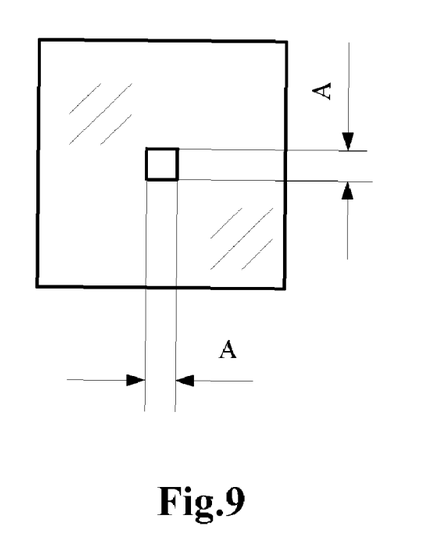
FIG. 9 is a sectional view of the flow chamber according to the embodiment of the present invention along line A-A of FIG. 8.

FIG. 8 shows how the sample liquid and sheath fluid to be detected flow in the flow chamber. The sample liquid S encased within the sheath fluid T flows therewith simultaneously through the interrogation zone of the flow chamber under pressure, maintaining a laminar current condition therebetween so that they do not interfere with each other. The sample liquid becomes quite narrow under the hydraulic focusing effect, the width thereof being about 10-20 μm. In this way, the cells suspended in the sample liquid and having a width similar to that of the sample liquid will be arranged in a row and pass the interrogation zone one by one. Therefore, there is a solution to the problem that the signals are superimposed together when multiple cells are passing the interrogation zone at one time and thereby fail to be distinguished. The guiding hole in the flow chamber comprises a rectifying segment 211, an accelerating segment 212 and a detecting segment 213. Introduced in from the rectifying segment 211, the sheath fluid forms a laminar current therein, accelerated by the accelerating segment 212, and at the detecting segment 213 passes through the guiding hole while encasing the sample liquid that is injected in via a sample injection needle. The side length of the section of the square guiding hole of the detecting segment 213 is about 100 μm-400 μm, and preferably 200 μm in the present embodiment, as shown in FIG. 9.

Figure 10:
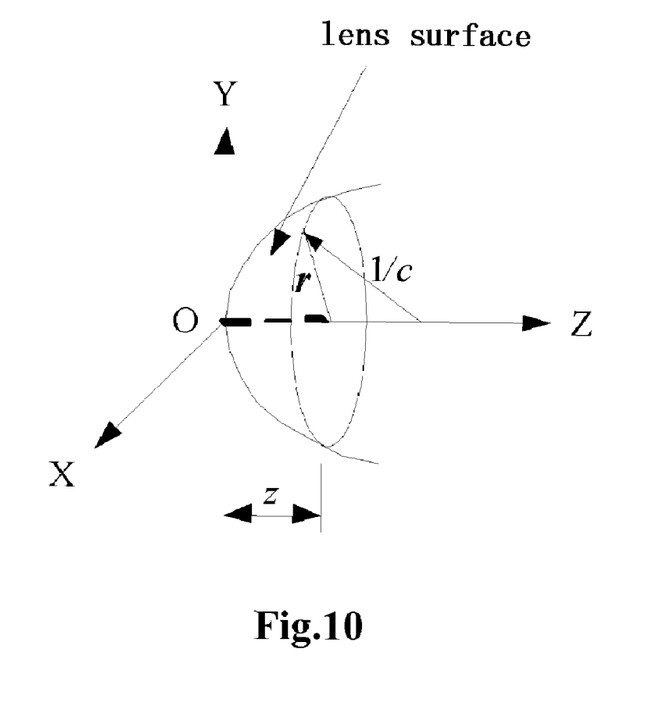
FIG. 10 is a schematic view showing the curved structure of the lens surface of the collimating lens according to the embodiment of the present invention.

121, which takes the form of an aspheric lens, preferably is about 0.3-0.5, and the shape of its lens surface is defined by the following formula:

$$z = \frac{cr^2}{1 + \sqrt{1 - (1+k)c^2 r^2}} + \alpha_1 r^2 + \alpha_2 r^4,$$

wherein, c is the curvature, z is the axial distance of the cross-section from the fixed point, k is a quadratic constant, and r is the radius of the cross-section.

In addition, the light beam shaping module 12 may comprise more than one aspheric collimating lens 121 with a numerical aperture no less than 0.3.

Figure 11:
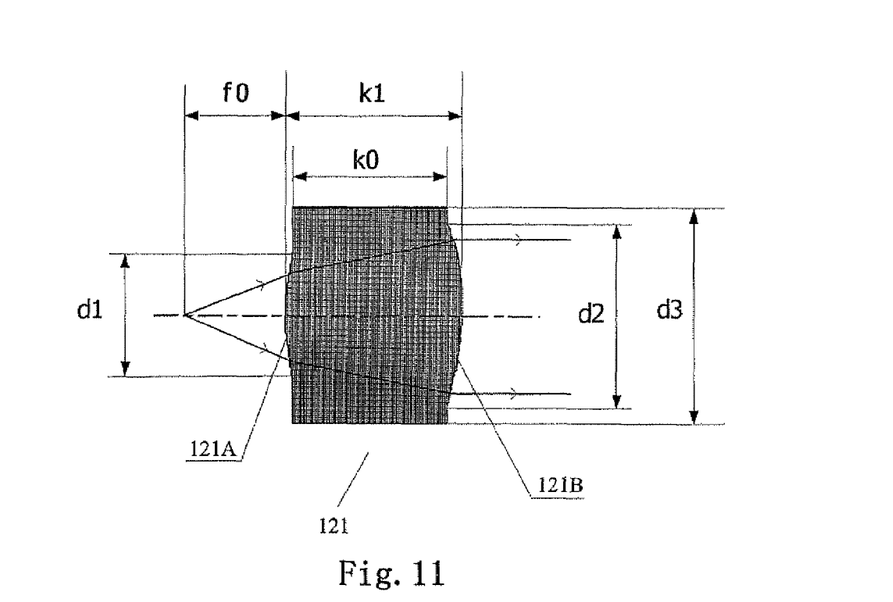
FIG. 11 is a structural schematic view of the collimating lens according to the embodiment of the present invention.

As shown in FIG. 11, the aspheric collimating lens 121 comprises a first lens surface 121A and a second lens surface 121B, wherein the first lens surface denotes the surface that the incident beam impinges on, and the parameters of the first lens surface 121A and second lens surface 121B are as follows:

|  | c | k | α1 | α2 |
|---|---|---|---|---|
| the first lens surface | 0.068609 | −87.228063 | 9.15754E−04 | −8.64353E−05 |
| the second lens surface | −0.231481 | −0.648067 | −1.65853E−04 | 8.28138E−06 |

The light beam generated by the illuminating unit 1 irradiates onto the detecting segment 213 of the flow chamber 21, and having passed through the light beam shaping module 12, forms an irradiated region of 20 μm (in the cell flowing direction)×10 μm (in the light beam transmitting direction)×200 μm (in the direction perpendicular to the plane which is defined by the cell flowing direction and the light beam transmitting direction) as mentioned above. Scattering will occur when cells pass through this region. The scattered light beam is then sent to the signal processing unit 3, which receives and correspondingly processes the scattered light beam passing through the flow chamber 21.

The signal processing unit 3 comprises a photoelectric detection module 31, a signal processing module 32 and an analysis module 33 which are connected in series, as shown in FIG. 4. The photoelectric detection module collects the scattered light in different angle ranges onto the photoelectric converter, which converts the optical signals into corresponding electrical signals and then transmits them to the signal processing module. The signal processing module extracts the peak or pulse width information from the signals and send these information to the analysis module. The analysis module counts and classifies the received signals to form a one-dimensional histogram or two-dimensional scattergram.

EXAMPLE 2

The second embodiment is a further improvement over the first one. To focus the Gauss light beam emitted by the semiconductor laser 11 and having a relatively large angle of divergence onto the interrogation zone of the flow chamber 21, the collimating lens 121 in the light beam shaping module 12 is an aspheric collimating lens with a large numerical aperture, the magnitude of which is at least 0.3. As shown in FIG. 10, the numerical aperture of the single collimating lens In the present embodiment, as shown in FIG. 11, the clear aperture d1 of the first lens surface 121A is 4.4 mm; the clear aperture d2 of the second lens surface 121B is 5.87 mm; the aperture d3 of the collimating lens 121 is 7.20 mm; the thickness k0 of the collimating lens 121 is 4.21 mm; the center-to-center distance k1 of the collimating lens 121 is 5.36 mm; and the distance f0 between the focal plane and the center of the first lens surface 121A is 3.44 mm.

Figure 14:
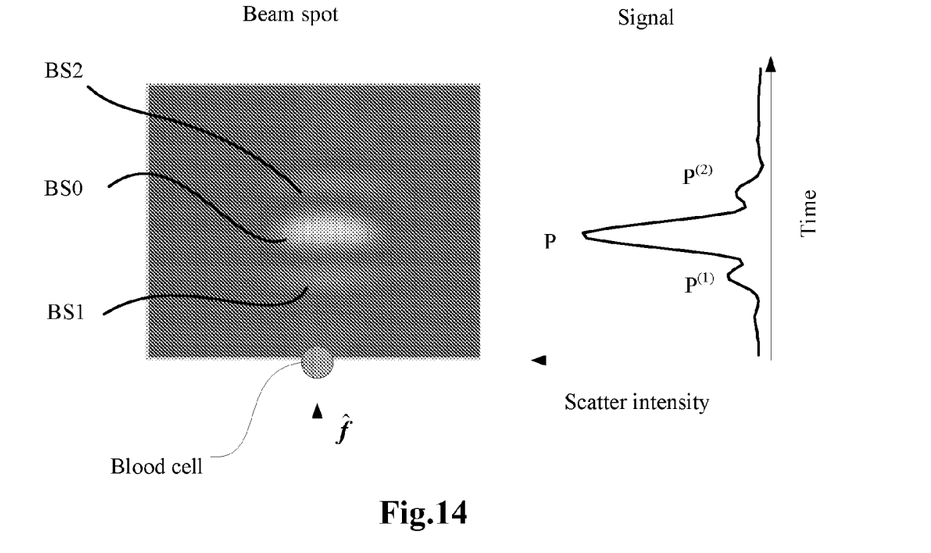
FIG. 14 shows the application of a scattered signal in prior art.
Figure 15:
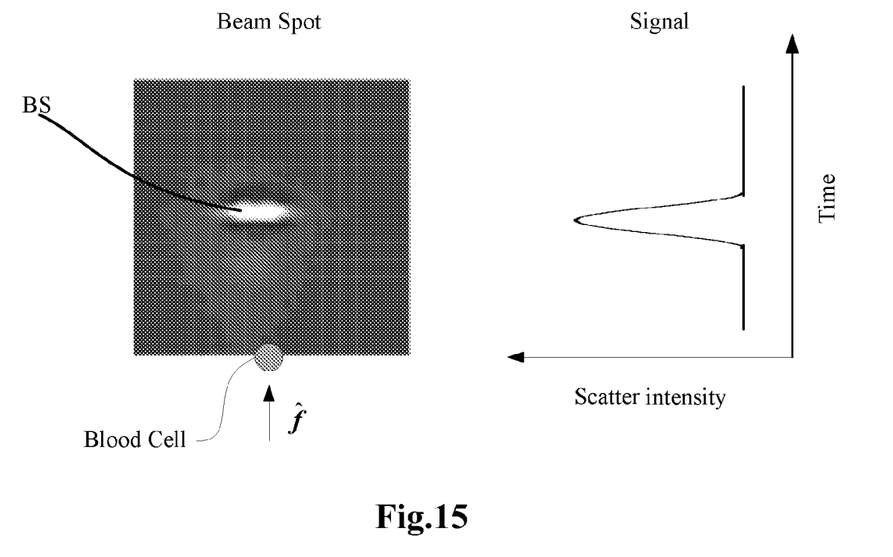
FIG. 15 shows the application of the scattered signal according to the embodiment of the present invention.

Thus, in the present embodiment, the collimating lens 121 with a numerical aperture up to 0.4 is used for effectively eliminating the spherical aberration by collimating or focusing the light beam with a 30° aperture angle. Its contribution to the present invention is to eliminate the above mentioned sidelobes of the spot so as to reduce the difficulty in the signal pulse recognition. FIG. 14 is a view showing a prior art scattered signal, in which the spot comprises sidelobes. FIG. 15 is a view showing the scattered signal obtained in the present embodiment, in which the sidelobes are eliminated, and the problem of accompanying pulse is resolved so that the difficulty of pulse recognition is reduced, thus the sample measurement is more accurate.

EXAMPLE 3

Figure 12:
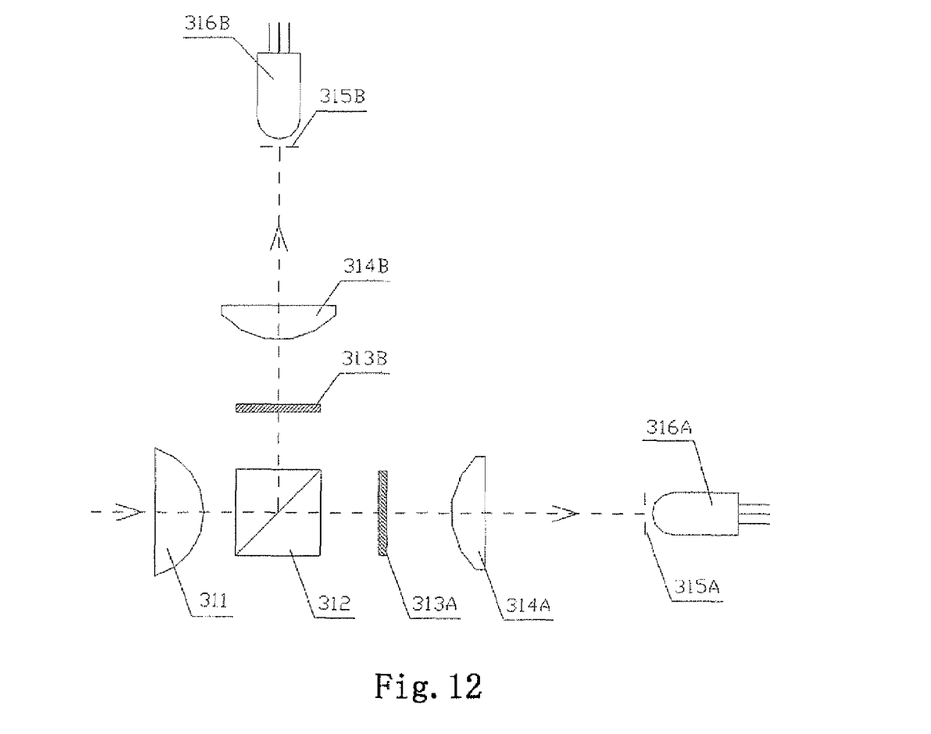
FIG. 12 is a structural schematic view of the photoelectric detection module according to the embodiment of the present invention.

The third embodiment is a further improvement over the first and second embodiments. In the present embodiment, as shown in FIG. 12, the photoelectric detection module 31 comprises two sets of photoelectric signal collecting sub-modules and corresponding photoelectric converters 316A 316B. These two sets of photoelectric signal collecting sub-modules respectively collect optical signals with different scattering angles, and the photoelectric converters perform corresponding photoelectric conversion for the optical signals. In particular, the photoelectric detection module 31 comprises a collimating lens 311, a light-splitting prism 312, annular diaphragms 313A, 313B, condensers 314A, 314B, pinhole diaphragms 315A, 315B and photoelectric converters 316A, 316B.

The photoelectric signal collecting sub-module is accordingly comprised of the annular diaphragms 313A, 313B and the condensers 314A, 314B, wherein the clear apertures of the annular diaphragms 313A and 313B are unequal, which may be employed respectively to collect the scattered light within different angle ranges.

In the present embodiment, the scattered light, after collimated by the collimating lens 311, is divided into two beams by the light-splitting prism 312. The range of the scattered light collected by the two sets of photoelectric signal collecting sub-modules is determined by the focal length of the collimating lens 311 and the clear apertures of the annular diaphragms 313A, 313B. For example, if the range of the scattered light to be collected is $[\theta_1, \theta_2]$, the clear aperture of the annular diaphragm 313A or 313B will be:

$$[F^*\tan\theta_1, F^*\tan\theta_2],$$

wherein F is the focal length of the collimating lens 311.

Figure 13:
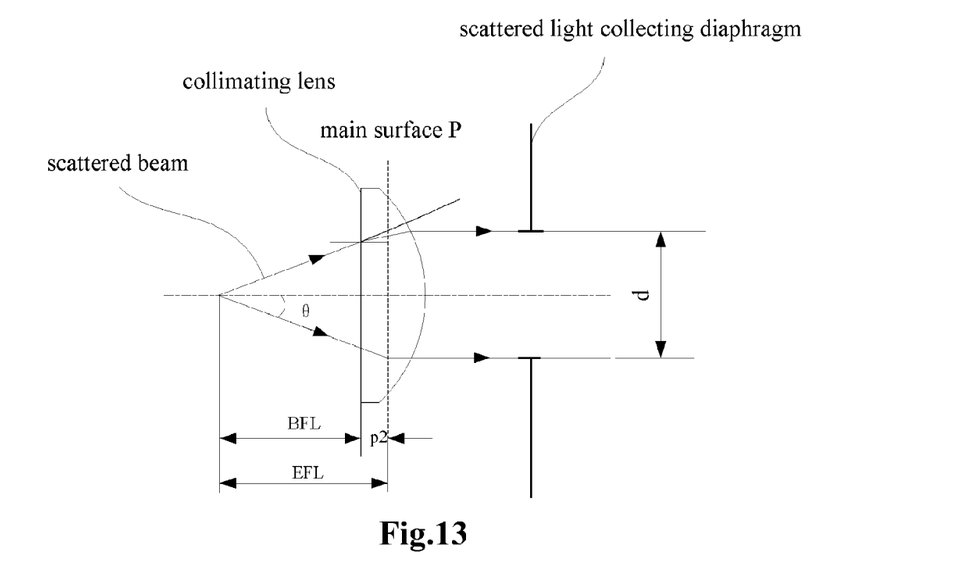
FIG. 13 is a schematic view showing the relationship between the collecting angle of the scattered light and the clear aperture of a diaphragm.

FIG. 13 shows the relation between the clear aperture and the angle of the scattered light to be collected, which is characterized as the clear aperture $d=2EFL\cdot\tan\theta$, wherein EFL is the effective focal length of the collimating lens.

For the collection of such scattered light with a rather large angle or irradiating spots, the collimating lens 311 may also individually use an aspheric lens with a large numerical aperture which is the same as or similar to that of the collimating lens 121, the numerical aperture of which is at least 0.4. The structure thereof is the same as or similar to that of the collimating lens 121, and is thereby omitted here.

These two sets of photoelectric signal collecting sub-modules respectively collect the scattered light in the range of 1-5°, referred to as small angle forward scattered light LAS, and the scattered light in the range of 8-20°, referred to as moderate angle forward scattered light MAS. These two beams of scattered light are respectively collected by the focusing lens to the photoelectric converters 316A, 316B for photoelectrical conversion and forming an electrical signal which is sent to the signal processing module 32.

The signal processing module amplifies and filters the photoelectrically converted electrical signal, digitizing the signal, then extracts the peak or pulse width information from the signal, and finally sends the information to the analysis module for analyzing. The analysis module analyzes each cell's peak or pulse width information of the two light beams, and then counts and classifies the cells based on the information. Further, the analysis module statistically analyzes all the cells of the blood sample to be detected and provides a characteristic judgement on the blood sample. The analysis module is also useful for outputting the result of analysis, and the output device may be a printer or LCD.

Figure 16:
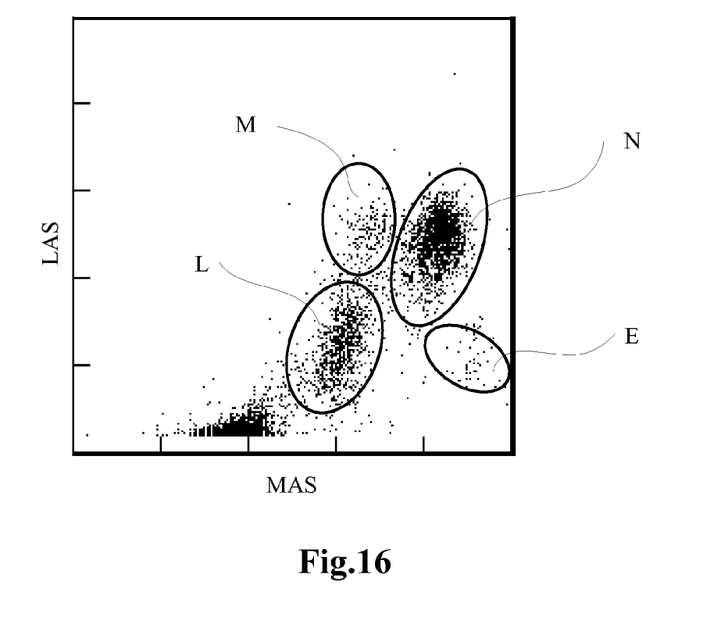
FIG. 16 shows the result of the test for white blood cells classification according to the embodiment of the present invention.

The system of the present invention is employed hereunder to measure the whole blood sample. FIG. 16 shows a scattergram plotted with the pulse peak values of LAS and MAS. As from the figure, using the LAS and MAS signals obtained with the flow cytometer of the present invention, the five subclasses of white cells may be classified into four groups, i.e., Group L consisting of lymphocytes, Group M consisting of monocytes, Group N consisting of neutrophilic granulocytes and basophils, and Group E consisting of eosinophils. This experiment proves the present invention to be feasible and effective.

What is claimed is:

1. A flow cytometer, comprising:
   a light source;
   a light beam shaping module for collimating and converging a light beam emitted from the light source so that the light beam thereby irradiates samples to be detected, wherein the light beam shaping module comprises an aspherical lens for collimating the light beam;
   a sample generation unit, which comprises a gas-liquid transfer controlling module and a flow chamber that are interconnected so that a sample liquid containing cells to be detected flows through the flow chamber while being carried by sheath fluid; and
   a signal processing unit, for collecting, photoelectrically converting, analyzing a scattered beam emitted from the flow chamber and outputting analysis results thereof, wherein
      a converged focus of the first cylindrical lens lies in an area where the sample flow passes through, while a converged focus of the second cylindrical lens is deviated from the area where the sample flow passes through,
      the light beam shaping module comprises a first cylindrical lens and a second cylindrical lens for respectively converging the light beams in two directions,
      a convergent light beam through the first and second cylindrical lenses have a cross section of an elliptical pattern in the cell-detection zone of the flow chamber, wherein
         a minor axis of the elliptical pattern being 15 µm-25 µm long,
         a major axis being 160 µm-220 µm long, and
         a direction of the minor axis being coincident with the flowing direction of the sample flow within the flow chamber, while a direction of the major axis perpendicular to the plane which is defined by the flowing direction of the sample flow and the transmitting direction of the light beam, and
      an irradiation depth of the light beams is 8 µm-12 µm, and a light intensity is uniformly distributed at a segment in the direction of the major axis.

2. The flow cytometer of claim 1, wherein converging directions of the first and second cylindrical lenses are perpendicular to each other.

3. The flow cytometer of claim 1, wherein:
   the first cylindrical lens converges the light beam in a flowing direction of sample flow, in which the first cylindrical lens is a positive cylindrical lens or a combination of more than one positive cylindrical lens, or a combination of at least one positive cylindrical lens and at least one negative cylindrical lens;
   the second cylindrical lens converges the light beam in a direction perpendicular to a plane defined by the flowing direction of the sample flow and a transmitting direction of the light beam, in which the second cylindrical lens is a positive cylindrical lens or a combination of more than one positive cylindrical lens, or a combination of at least one positive cylindrical lens and at least one negative cylindrical lens.

4. The flow cytometer of claim 1, wherein the major axis of the elliptical pattern has a length that is substantially equal to the width of an inner wall of the cell-interrogation zone of the flow chamber.

5. The flow cytometer of claim 1, wherein the aspherical lens has a large numerical aperture with a value of about 0.3 or larger and is disposed on a light path running from the light source through the cylindrical lens.

6. The flow cytometer of claim 5, wherein:
the aspherical lens comprises a first lens surface and a second lens surface, wherein an incident light beam impinges on the first lens surface; and
at least one of the first lens surface and the second lens surface of the first aspheric collimating lens satisfies the following formula:

$$z = \frac{cr^2}{1+\sqrt{1-(1+k)c^2r^2}} + \alpha_1 r^2 + \alpha_2 r^4,$$

wherein
c is a curvature,
z is an axial distance of a cross-section from a fixed point,
k is a quadratic constant,
r is a radius of the cross-section, and
c, z, k, and r of the first lens surface and second lens surface are configured as follows:

|  | c | k | α1 | α2 |
|---|---|---|---|---|
| the first lens surface | 0.068609 | −87.228063 | 9.15754E−04 | −8.64353E−05 |
| the second lens surface | −0.23148106 | −0.648067 | −1.65853E−04 | 8.28138E−06. |

7. The flow cytometer of claim 1, wherein:
the signal processing unit comprises a photoelectric detection module, a signal processing module, and an analysis module which are connected in series, wherein
the photoelectric detection module is configured for collecting light beams scattered in different ranges of angles into the photoelectric converter so that optical information of the light beams is converted into a corresponding electrical signal which is then sent to the signal processing module,
the signal processing module is configured for extracting a peak of a pulse width information from the corresponding electrical signal and sending the peak or the pulse width information to the analysis module, and
the analysis module is configured for counting and classifying received signals to form a one-dimensional or two-dimensional plot.

8. The flow cytometer of claim 7, wherein the photoelectric detection module comprises two sets of photoelectric signal collecting sub-modules for respectively collecting optical signals with different scattering angles and corresponding photoelectric converters for converting the optical signals into the corresponding electrical signals.

9. The flow cytometer of claim 7, wherein the photoelectric detection module comprises at least one second aspherical collimating lens for collimating the light beams emitted from the flow chamber, wherein the numerical aperture of the second aspherical collimating lens has a value of about 0.4 or larger.

10. The flow cytometer of claim 1, wherein the light source comprises a semiconductor laser.

11. An optical system for use in a flow cytometer, comprising:
a light source; and
a light beam shaping module for collimating and converging light beams emitted from the light source, wherein
the light beam shaping module comprises a first cylindrical lens and a second cylindrical lens for respectively converging the light beams in two directions,
the light beans shaping module comprises an aspherical lens lot collimating the light beams,
a converged focus of the first cylindrical lens deviates from that of the second cylindrical lens,
the light beams converged by the first and second cylindrical lenses have a cross section of an elliptical pattern in a converging zone, a minor axis of the elliptical pattern being about 15 μm-25 μm long, and a major axis being about 160 μm-220 μm long, and
an irradiation depth of the light beams is about 8 μm-12 μm, and a light intensity is substantially uniformly distributed at a segment in a direction of the major axis.

12. The optical system of claim 11, wherein the converging directions of the first and second cylindrical lenses are perpendicular to each other.

13. The optical system of claim 11, wherein:
the first cylindrical lens is a positive cylindrical lens, a combination of more than one positive cylindrical lens, or a combination of at least one positive cylindrical lens and at least one negative cylindrical lens; and
the second cylindrical lens is a positive cylindrical lens, a combination of more than one positive cylindrical lens, or a combination of at least one positive cylindrical lens and at least one negative cylindrical lens.

14. The optical system of claim 11, wherein the aspherical lens has a large numerical aperture and is disposed on a light path running from the light source through the cylindrical lens.

15. The optical system of claim 14, wherein the numerical aperture of the aspherical lens has a value of about 0.3 or larger.

16. The optical system of claim 14, wherein:
the aspherical lens comprises a first lens surface and a second lens surface, wherein an incident beam impinges on the first lens surface; and
at least one of the first lens surface and the second lens surface of the aspheric collimating lens satisfy the following formula:

$$z = \frac{cr^2}{1+\sqrt{1-(1+k)c^2r^2}} + \alpha_1 r^2 + \alpha_2 r^4,$$

wherein
c is a curvature,
z is a axial distance of a cross-section from a fixed point,
k is a quadratic constant,
r is a radius of the cross-section, and
c, z, k, r of the first lens surface and seconds lens surface are configured as follows:

|  | c | k | α1 | α2 |
|---|---|---|---|---|
| the first lens surface | 0.068609 | −87.228063 | 9.15754E−04 | −8.64353E−05 |
| the second lens surface | −0.23148106 | −0.648067 | −1.65853E−04 | 8.28138E−06. |

\* \* \* \* \*